United States Patent [19]

Zawistowska

[11] Patent Number: 4,910,297

[45] Date of Patent: Mar. 20, 1990

[54] ALPHA-AMYLASE INHIBITOR

[75] Inventor: Urszula Zawistowska, Winnipeg, Canada

[73] Assignee: ABI Biotechnology Inc., Winnipeg, Canada

[21] Appl. No.: 207,669

[22] Filed: Jun. 16, 1988

[30] Foreign Application Priority Data

Jun. 29, 1987 [CA] Canada .................................. 540780

[51] Int. Cl.$^4$ ........................... C07K 15/10; A23J 1/12
[52] U.S. Cl. ....................................... 530/375; 426/27; 426/549; 426/622; 530/372; 530/374
[58] Field of Search ....................... 530/375, 374, 372; 426/27, 549, 622

[56] References Cited

U.S. PATENT DOCUMENTS

| 3,944,537 | 3/1976 | Saunders et al. | 530/375 |
| 3,950,319 | 4/1976 | Schmidt et al. | 530/375 X |
| 4,634,763 | 1/1987 | Sugiyama et al. | 530/375 |
| 4,806,626 | 2/1989 | Maeda et al. | 530/375 |

OTHER PUBLICATIONS

Weselake et al. (1983) *Plant Physiol* 72:809-812.
Mundy et al. (1983) *Carlob Res Comm* 48:81-90.
"Principles of Biochemistry, Fifth Edition" (A. White, McGraw-Hill Inc., 1973), Chapter 6, pp. 136-137.
Meredith and Pomeranz (1984), Advances in Cereal Science and Technology, pp. 239-287, AACC, St. Paul, MN.
Svendson et al., *Carlsberg Res. Comm.* (1986) 51:43-50.
Mundy et al., *FEBS Lett.* (1984) 167:210-214.
Maeda, Koji, *Biochim. Biophys. Acta.* (1986) 871:250-256.
Weselake et al., *Cereal Chem.* (1985) 62:120-123.
Weselake and Hill, *Cereal Chem.* (1983) 60:98-101.
Zawistowska, U. et al., *Cereal Chem.* (1988) Preprint.

*Primary Examiner*—Howard E. Schain
*Attorney, Agent, or Firm*—Irell & Manella

[57] ABSTRACT

A novel procedure for the preparation of a protein which is an inhibitor of alpha-amylase II is described. The protein may be prepared by extracting barley meal with a Tris-HCl buffer and purifying the crude inhibitor thus obtained by a chromatographic procedure. Alternatively, the protein may be prepared by recombinant DNA techniques. The protein can be applied as an additive to sprout-damaged wheat flour which can then be used to provide improved quality bread.

7 Claims, 2 Drawing Sheets

Ala-Asp-Pro-Pro-Pro-Val-His-Asp-Thr-Asp-Gly-His-Glu-Leu-Arg-
Ala-Asp-Ala-Asn-Tyr-Tyr-Val-Leu-Ser-Ala-Asn-Arg-Ala-His-Gly-
Gly-Gly-Leu-Thr-Met-Ala-Pro-Gly-His-Gly-Arg-His-Cys-Pro-Leu-
Phe-Val-Ser-Gln-Asp-Pro-Asn-Gly-Gln-His-Asp-Gly-Phe-Pro-Val-
Arg-Ile-Thr-Pro-Tyr-Gly-Val-Ala-Pro-Ser-Asp-Lys-Ile-Ile-Arg-
Leu-Ser-Thr-Asp-Val-Arg-Ile-Ser-Phe-Arg-Ala-Tyr-Thr-Thr-Cys-
Leu-Gln-Ser-Thr-Glu-Trp-His-Ile-Asp-Ser-Glu-Leu-Ala-Ala-Gly-
Arg-Arg-His-Val-Ile-Thr-Gly-Pro-Val-Lys-Asp-Pro-Ser-Pro-Ser-
Gly-Arg-Glu-Asn-Ala-Phe-Arg-Ile-Glu-Lys-Tyr-His-Gly-Ala-Glu-
Val(Ser)Glu-Tyr-Lys-Leu-Met-Ser-Cys-Gly-Asp-Trp-Cys-Gln-Asp-
Leu-Gly-Val-Phe-Arg-Asp-Leu-Lys-Gly-Gly-Ala-Trp-Phe-Leu-Gly-
Ala-Thr-Glu-Pro-Tyr-His-Val-Val-Val-Phe-Lys-Lys-Ala-Pro-Pro-
Ala

FIG. I

ALPHA-AMYLASE INHIBITOR

TECHNICAL FIELD OF THE INVENTION

This invention relates to the preparation of an alpha-amylase inhibitor that is purified from cereal grains or is produced using recombinant DNA techniques. This protein is effective in inhibiting the activity of alpha-amylase II, the major constituent of alpha-amylase in germinated wheat, and it is therefore useful in improving the bread making quality of flour obtained from sprouted wheat.

BACKGROUND OF THE INVENTION

It is known that sprouted wheat produces a poorer quality of flour compared with that obtained from unsprouted wheat. When such poorer quality flour is used in the baking of bread, the bread so obtained has a certain stickiness and this causes trouble when slicing machines are used to slice loaves of such bread. Sprouting of wheat is associated with an increase in the amount of the alpha-amylase II, a starch degrading enzyme.

Since the increased level of alpha-amylase is a major factor associated with wheat sprouting, it has been implied by different authors that it should be possible to improve baking properties of sprout-damaged wheat flour by reducing alpha-amylase activity. A number of different physico-chemical (increased temperature, low pH) and chemical (surfactants, heavy metals, chelators) factors have been studied as potential alpha-amylase inhibitors or inactivators as reviewed by Meredith and Pomeranz, (1984) in Advances in Cereal Science and Technology (Y. Pomeranz, ed.), pages 239-320, AACC, St. Paul, Minn.

A number of the investigated factors were found to suppress alpha-amylase effects. However, some of them affected not only alpha-amylase but also sensitive gluten proteins by changing their structure and functional properties important for baking performance and caused deterioration of other technological characteristics of bread. Moreover, the application of different chemicals such as alpha-amylase inhibitors inactivators studied as food additives is limited due to the toxicity of some of them. Therefore, an application of a non-toxic alpha-amylase inhibitor that could be safely added to the flour from sprouted wheat to eliminate an excess of alpha-amylase activity would be very much desirable.

SUMMARY OF THE INVENTION

The present invention lies in the discovery that an alpha-amylase inhibitor can be isolated from cereal grains such as barley, and purified to provide the protein in an improved yield compared with known procedures. It has also been found that this barley protein, which is an inhibitor of alpha-amylase II, may be added to flour prepared from sprouted wheat and the protein-containing flour thus obtained may thereafter be used to prepare improved quality bread.

The barley protein with which this invention is concerned is an alpha-amylase II inhibitor having the following physical and chemical characteristics: it is a salt soluble protein with molecular weight of about 21,000 and isoelectric point at pH 7.2; it inhibits wheat alpha-amylase II and subtilisin (alkaline protease from Bacillus subtilis); and it does not inhibit the human serine proteases trypsin and chymotrypsin. The protein may be purified from its native source or produced using recombinant DNA techniques.

According to a preferred embodiment of the invention, a process is provided for the isolation and purification of a barley protein, which is an alpha-amylase II inhibitor isolated from barley meal. The process comprise extracting barley meal with an aqueous buffer of appropriate pH range to provide an extract of crude inhibitor and then purifying the crude inhibitor thus obtained by means of a chromatographic procedure.

Another aspect of the invention is a novel wheat flour composition comprising sprout-damaged wheat flour in admixture with the barley protein which is an alpha-amylase inhibitor.

A further aspect of the invention is an improved process for preparing baked products from spout-damaged wheat flour, wherein the improvement comprises adding to the sprout-damaged wheat flour an amount of a natural, non-toxic alpha-amylase inhibitor effective to suppress excessive activity of alpha-amylase II present in the sprout-damaged wheat flour without affecting gluten proteins.

BRIEF DESCRIPTION OF THE DRAWINGS

FIG. 1 shows the amino acid sequence of the barley alpha-amylase inhibitor (Svendsen et al, *Carlsberg Res Comm* (1986) 51:43-50.

MODES FOR CARRYING OUT THE INVENTION

Figure 2:
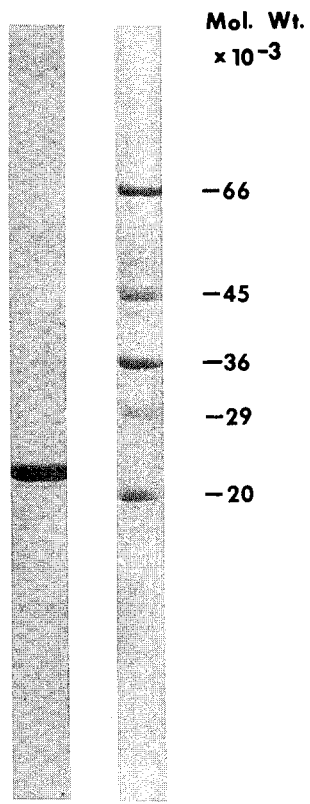
FIG. 2 presents sodium dodecyl sulfate polyacrylamide gel electrophoretic (SDS-PAGE) pattern of alpha-amylase II inhibitor isolated from barley cv. Bonanza and purified by Cu-IDA-Sepharose 6B chromatography followed by ion exchange chromatography on S-Sepharose Fast Flow. SDS-PAGE was performed in non-reducing conditions on gradient gels (10-18%) using Laemmli (*Nature* (1970) 227:680-685) discontinuous system. Lanes: 1, barley inhibitor; 2, the molecular weight protein standards are (from top to bottom): bovine serum albumin, ovalbumin, gluteraldehyde-3-phosphate dehydrogenase, bovine carbonic anhydrase and soybean trypsin inhibitor (Sigma Chemical Company, St. Louis, Mo., USA). Approximately 16 $\mu$g of protein was applied per lane.

The natural alpha-amylase inhibitors are low molecular weight (~20,000 daltons), salt soluble proteins present in the endosperm of barley, wheat, rye and triticale, and possibly other cereals. These proteins inhibit the activity of the high isoelectric point (6.0-6.5) alpha-amylases comprising more than 84% of total alpha-amylase activity of germinated cereal grains. The inhibitors isolated from barley and wheat have almost identical amino acid composition (Mundy et al, *FEBS Lett* (1984) 167:210-214) and the amino acid sequence have been determined by Svendsen et al, (1986) supra, and Maeda, *Biochim Biophys Acta* (1986) 871:250-256, respectively. Barley is the preferred source of the inhibitor since anti-alpha-amylase activity in barley is several-fold higher than in wheat, rye and triticale (Weselake et al, *Cereal Chem* (1985) 62:120–123).

The aqueous buffer used in the process of this invention is preferably Tris-HCl, a well-known buffer used in the art. Tris is a trivial name standing for tris(hydroxymethyl)-aminomethane. The Tris-HCl buffer to be used may be varied according to the molarity of the solution which may be adjusted for the desired pH of the buffer to be used by the addition of hydrochloric acid, if necessary. Thus, for example, for the extraction procedure involving barley meal, the Tris-HCl buffer to be used may have a concentration of from about 0.05M to about 0.1M, preferably about 0.05M, while the pH of the Tris-HCl buffer to be used may be from about 5.5 to about 8.0, preferably about 5.5.

The purification by means of a chromatographic procedure may be carried out by employing a two-step procedure using first immobilized metal affinity chromatography followed by ion exchange chromatography.

Affinity chromatography is carried out using a copper-iminodiacetic acid (IDA)-non-ionic gel resin. Such resins include Bio-Gel A-1.5M (Bio-Rad), Sephacryl S-300, Sepharose Cl-6B, Cl-4B, Cl-2B, 6B, 4B, 2B as well as Sepharose 6 (Pharmacia) and Ultrogel AcA 22 (LKB), Matrex Cellufine GLC 2000 and GC 700 (Amicon, USA) Toyopearl HW-65F (Toyo Soda, Japan), Trisacryl GF 2000 LS (IBF, France), Macrosorb KGAX, K4AX, and K2AX (Sterling Organics, UK), and Eupergit C and C250L (Rohm Pharma, FRG). The preferred matrix employs Sepharose 6B.

For ion-exchange chromatography, cation exchange marrixes such as carboxymethyl-Sepharose and suphonate(S)-Sepharose columns may be employed. A strong cation exchange type of matrix such as S-Sepharose (Fast Flow) from Pharmacia is preferred.

The novel wheat flour composition comprises sprout-damaged wheat flour in admixture with the barley alpha-amylase II inhibitor. The concentration of said inhibitor in the flour is preferably within the range of from about 0.02 g to about 5 g of protein per kg of wheat flour.

It is to be understood that the amount of protein used as inhibitor to be added to the sprout-damaged wheat flour will depend essentially on the degree of sprout-damage of the wheat, i.e. the amount of damage formed during the number of days that the wheat was allowed to germinate before being harvested. It may generally be found that use of from about 2 g to about 4 g of the protein, and preferably about 3 g of the protein, per kg of wheat flour is effective. A smaller or larger amount of this protein may be used in the wheat flour according to the quality or content of alpha-amylase of the flour.

Standard Methods

Most of the techniques which are used to isolate cDNA, construct oligonucleotides, perform site-specific mutagenesis, construct vectors, transform cells, and the like are widely practiced in the art, and most practitioners are familiar with the standard resource materials which describe specific conditions an procedures. However, for convenience, the following paragraphs may serve as a guideline.

Cloning the Gene Encoding the Alpha-Amylase Inhibitor

The alpha-amylase inhibitor may be synthetic or natural, or combinations thereof. A natural inhibitor gene (or portion thereof) may be obtained by preparing a barley cDNA or genomic library and screening for the presence of the inhibitor gene. Preparation of cDNA libraries from a messenger RNA population is well known and described fully in Huynh et al (1984) in DNA Cloning, Vol. 1: A Practical Approach (D. Glover, ed.), pp. 49–78, IRL Press, Oxford. Generally, if the library is to be screened by hybridization with a nucleotide probe, any insertion vector is appropriate but lambda-gt10 is preferred as it permits direct selection against nonrecombinant phages. If the library is to be screened by use of antibody probes, the most commonly used expression vector is lambda-gt11, in which the cloned coding sequences are fused to coding sequences for beta-galactosidase.

Screening may be accomplished using labeled DNA probes specific for the polypeptide or using antibodies for the gene product. Both methods are conventional and well described in the literature. Suitable antibodies may be prepared for purified alpha-amylase inhibitor obtained from barley cultivar Bonanza as exemplified in the Experimental section hereinafter. Suitable DNA probes may be obtained based on the amino acid sequence of the inhibitor, or based on a nucleotide sequence deduced therefom.

When preparing a synthetic nucleotide sequence, it may be desirable to modify the natural nucleotide sequence. For example, it will often be preferred to use codons which are preferentially recognized by the desired host. When employing a yeast host, codons which appear at high frequency in the structural genes encoding the yeast glycolytic enzymes may be employed. In some instances, it may be desirable to further alter the nucleotide sequence to create or remove restriction sites to, for example, enhance insertion of the gene sequence into convenient expression vectors or to substitute one or more amino acids in the resulting polypeptide to increase stability.

Synthetic oligonucleotides are prepared by either the phosphotiester method as described by Edge et al, *Nature* (supra) and Duckworth et al, *Nucleic Acids Res* (1981) 9:1691 or the phosphoramidite method as described by Beaucage, S. L., and Caruthers, M. H., *Tet Letts* (1981) 22:1859 and Matteucci, M. D., and Caruthers, M. H., *J Am Chem Soc* (1981) 103:3185, and can be prepared using commercially available automated oligonucleotide synthesizers.

Hosts and Control Sequences

Both procaryotic and eucaryotic systems may be used to express the alpha-amylase inhibitor encoding sequences; procaryotic hosts are, o course, the most convenient for cloning procedures. The vectors may be single copy or low or high multicopy vectors. Procaryotes most frequently are represented by various strains of *E. coli;* however, other microbial strans may also be used. Plasmid vectors which contain replication sites, selectable markers and control sequences derived from a species compatible with the host are used; for example, *E. coli* is typically transformed using derivatives of pBR322, a plasmid derived from an *E. coli* species by Bolivar et al, *Gene* (1977) 2:95. pBR322 contains genes for ampicillin and tetracycline resistance, and thus provides multiple selectable markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang et al, *Nature* (177) 198:1056), the tryptophan (trp) promoter system (Goeddel et al, *Nucleic Acids Res* (1980) 8:4057), the lambda-derived $P_L$ promoter (Shimatake et al, *Nature* (1981) 292:128) and N-gene ribosome binding site, and the trp-lac (trc) promoter system (Amann and Brosius, *Gene* (1985) 40:183).

In addition to bacteria, eucaryotic microbes, such as yeast, may also be used as hosts. Laboratory strains of *Saccharomyces cerevisiae*, baker's yeast, are most used although a number of other strains or species are commonly available. Vectors employing, for example, the 2 [mu] origin of replication of Broach, J. R., *Meth Enz* (1983) 101:307, or other yeast compatible origins of replication (see, for example, Stinchcomb et al, *Nature* (1979) 282:39, Tschumper, G., et al, *Gene* (1980) 10:157 and Clarke, L., et al, *Meth Enz* (1983) 101:300) may be used.

Control sequences for yeast vectors include promoters for the synthesis of glycolytic enzymes (Hess et al, *J Adv Enzyme Reg* (1968) 7:149; Holland et al, *Biochemistry* (1978) 17:4900). Additional promoters known in the art include the promoter for 3-phosphoglycerate kinase (Hitzeman et al, *J Biol Chem* (1980) 255:2073). Other promoters, which have the additional advantage of transcription controlled by growth conditions and/or genetic background are the promoter regions for alcohol dehydrogenase 2, isocytochrome C, acid phosphatase, degradative enzymes associated with nitrogen metabolism, the alpha factor system and enzymes responsible for maltose and galactose utilization. It is also believed terminator sequences are desirable at the 3' end of the coding sequences. Such terminators are found in the 3' untranslated region following the coding sequence in yeast-derived genes.

The vector may include two replication systems, allowing for maintenance of the replicon in both a yeast host for expression, and in a procaryotic (e.g., *E. coli*) host for cloning. Examples of such yeast-bacteria shuttle vectors include YEp24 (Botstein et al, *Gene* (1979) 8:17–24), pCl/1 (Brake et al, *Proc Natl Acad Sci USA* (1984) 81:4642–4646), and YRp17 (Stinchcomb et al, *J Mol Biol* (1982) 158:157).

The selection of suitable yeast and other microorganism hosts (e.g., diploid, haploid, auxotrophs, etc.) for the practice of the present invention is within the skill of the art. When selecting yeast hosts for expression, suitable hosts may include those shown to have, inter alia, good secretion capacity, low proteolytic activity, and overall robustness. Yeast and other micrgorganisms are generally available from a variety of sources, including the Yeast Genetic Stock Center, Department of Biophysics and Medical Physics, University of California, Berkeley, Calif.; and the American Type Culture Collection, Rockville, Md.

Host strains available for use in cloning and bacterial expression herein include *E. coli* strains such as MC1061, DH1, RR1, B, C600hfl, K803, HB101, JA221, and JM101.

Transformations

Depending on the host cell used, transformation is done using standard techniques appropriate to such cells. The calcium treatment employing calcium chloride, as described by Cohen, S. N., *Proc Natl Acad Sci USA* (1972) 69:2110, or the $RbCl_2$ method described in Maniatis et al, *Molecular Cloning: A Laboratory Manual* (1982) Cold Spring Harbor Press, p. 254 and Hanahan, D., *J Mol Biol* (1983) 166:557–580 may be used for procaryotes or other cells which contain substantial cell wall barriers.

There are a wide variety of ways to transform yeast. For example, spheroplast transformation is taught, for example, by Hinnen et al, *Proc Natl Acad Sci USA* (1978) 75:1919–1933, and Stinchcomb et al, EPO Publication No. 45,573. Transformants are grown in an appropriate nutrient medium, and, where appropriate, maintained under selective pressure to ensure retention of endogenous DNA. Where expression is inducible, growth can be permitted of the yeast host to yield a high density of cells, and then expression is induced. The secreted, processed non-yeast protein can be harvested by any conventional means, and purified by chromatography, electrophoresis, dialysis, solvent-solvent extraction, and the like.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

The DNA sequences which form the vectors are available from a number of sources. Backbone vectors and control systems are generally found on available "host" vectors which are used for the bulk of the sequences in construction. For the pertinent coding sequence, initial construction may be, and usually is, a matter of retrieving the appropriate sequences from cDNA libraries, genomic DNA libraries, or deposited plasmids. However, once the sequence is disclosed it is possible to synthesize the entire gene sequence in vitro starting from the individual nucleoside derivatives. The entire gene sequence for genes of sizable length, e.g., 500–1000 bp may be prepared by synthesizing individual overlapping complementary oligonucleotides and filling in single-stranded nonoverlapping portions using DNA polymerase in the presence of the deoxyribonucleotide triphosphates. This approach has been used successfully in the construction of several genes of known sequence. See, for example, Edge, M. D., *Nature* (1981) 292:756; Nambair, K. P., et al, *Science* (1984) 223:1299; Jay, *J Biol Chem* (1984) 259:6311.

Once the components of the desired vectors are thus available, they can be excised and ligated using standard restriction and ligation procedures.

In vector construction employing "vector fragments", the vector fragment is commonly treated with bacterial alkaline phosphatase (BAP) or calf intestinal alkaline phosphatase (CIP) in order to remove the 5' phosphate and prevent self-ligation of the vector. Alternatively, religation can be prevented in vectors which have been double digested by additional restriction enzyme digestion and separation of the unwanted fragments.

For portions of vectors derived from cDNA or genomic DNA which require sequence modifications, site specific mutagenssis may be used (Zoller, M. J., and Smith, M. *Nucleic Acids Res* (1982) 10:6487-6500 and Adelman, J. P., et al, *DNA* (1983) 2:183-193). This is conducted using a primer synthetic oligonucleotide primer complementary to a single-stranded phage DNA to be mutagenized except for limited mismatching, representing the desired mutation.

Verification of Construction

In the constructions set forth below, correct ligations for plasmid construction are confirmed by first transforming *E. coli* or other suitable hosts with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci USA* (1969) 62:1159, optionally following chloramphenicol amplification (Clewell, D. B., *J Bacteriol* (1972) 110:667). Several mini DNA preps are commonly used, e.g., Holmes, D. S., et al, *Anal Biochem* (1981) 114:193-197 and Birnboim, H. C., et al, *Nucleic Acis Res* (1979) 7:1513-1523. The isolated DNA is analyzed by dot blot analysis as described by Kafatos, F. C., et al, *Nucl Acid Res* (1977) 7:1541-1552, restriction enzyme analysis, or sequenced by the dideox nucleotide method of Sanger, F., et al, *Proc Natl Acad Sci USA* (1977) 74:5463, as further described by Messing et al, *Nucleic Acids Res* (1981) 9:309, or by the method of Maxam et al, *Methods in Enzymology* (1980) 65:499.

EXAMPLES

The following examples are provided for illustrative purposes only, and are not intended to limit the scope of the present invention.

EXAMPLE 1

Isolation and Purification of Alpha-Amylase II Inhibitor From Barley Grains

Barley (cv. Bonanza) kernels were dehusked for 20 seconds in a pearling machine and ground to a meal in a Cyclone Saple Mill, model MS (Udy Corp., Fort Collins, Colo., U.S.A.). 1 kg of barley meal was extracted with 4 l of 0.05M Tris-HCl buffer pH 5.5 at 4° C. for 60 minutes by stirring. After centrifugation for 20 minutes at 13,000×g at 4° C., the pH of the supernatant solution was adjusted with 1M NaOH to pH 7.5 and sodium chloride was added to reach concentration of 0.15M NaCl. The precipitate formed was left for 1 hour at 4° C. and removed by centrifugation for 30 minutes at 13,000×g at 4° C. The supernatant was additionally filtered, if required, through 5μ *Sartorius membranes (Sartorius, GMBH Gottingen, West Germany) and used for further purification.

A two-step procedure was employed for purification of the inhibitor:

1. Immobilized metal affinity chromatography on copper-IDA-non-ionic gel resin such as *Sepharose 6B (Pharmacia), followed by 2. Ion exchange chromatography on a cation exchange resin such as S-*Sepharose Fast Flow.

Immobilized Metal Affinity Chromatography

*Sepharose 6B was activated using epoxy-activation procedure of Sundberg and Porath, *J Chrom* (1974) 90:87-98. Coupling of IDA to epoxy-activated *Sepharose 6B was performed according to Porath, J., et al, *Nature* (1975) 258:598-599.

The two column system was used for inhibitor purification: a working column, 5×14.5 cm and a guard column, 5×9 cm. Both columns were packed with IDA-*Sepharose 6B gel equilibrated with deionized water and washed with 6 bed volumes of deionized water. The working column was then loaded with cupric sulfate solution containing 6 mg $CuSO_4.5H_2O$/ml until the blue color of copper ions was detectable in the eluate and then washed with 6 bed volumes of deionized water. Both columns were separately equilibrated overnight with 0.05M Tris-HCl buffer pH 7.5 containing 0.15M NaCl and connected together.

The supernatant from 1 kg of barley meal, prepared as described above, was applied to the Cu-IDA-*Sepharose 6B/IDA-*Sepharose 6B column tandem with the flow rate 126 ml/h, then columns were washed subsequently with:

1. 0.05M Tris-HCl buffer pH 7.5, 0.15M NaCl (equilibration buffer), and 2. 0.05M glycine in equilibration buffer, in that order.

In order to remove other proteins bound to Cu-IDA-*Sepharose 6B, washing with each of the above buffers was continued until absorbance at 280 nm was negligible. Inhibitor protein was eluted with equilibration buffer containing 0.200M glycine. Fractions containing inhibitor activity were combined, concentrated and dialyzed against deionized water on *Minitan (Canada Millipore Ltd., Mississauga, Ontario) using a 10,000 MW cut off membrane.

Ion Exchange Chromatography

The concentrated Cu-IDA-*Sepharose 6B-purified inhibior was dialyzed in *Spectrapor membrane tubing with 6000-8000 MW cut-off (Fisher Scientific, Winnipeg, Manitoba), against 0.025M Tris-HCl, pH 6.8 and the dialyzate was applied to a 5×15.5 cm S-*Sepharose Fast Flow column equilibrated with the same buffer. The column was eluted with a flow rate of 220 ml/h with equilibration buffer, followed with a gradient including 900 ml of 0.025M Tris-HCl, pH 6.8 and 900 ml of 0.025M Tris-HCl, 0.4M NaCl, pH 6.8. Fractions containing the inhibitor were combined and dialyzed against deionized water. The dialyzate was then centrifuged at 13,000×g for 20 minutes and the supernatant was freeze-dried.

Figure 3:
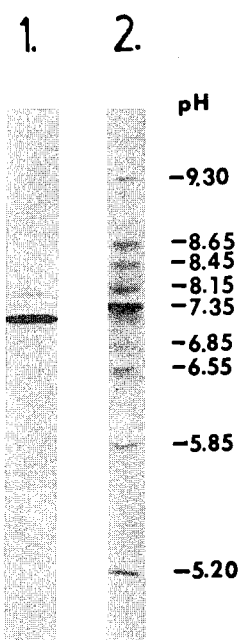
FIG. 3 shows isoelectric focusing (IEF) pattern of barley inhibitor purified as described in FIG. 2 IEF was carried out according to Zawistowska et al, *Cereal Chem* (1988) 65:413. Lanes: 1, barley inhibitor; 2, the isoelectric point protein standards (Pharmacia Canada Inc., Dorval, Canada) are (from top to bottom): trypsinogen, lentil lectin: -basic, -middle, and -acidic band, human carbonic anhydrase B, bovine carbonic anhydrase B, and beta-lactoglobulin A. Approximately 30 $\mu$g of protein was applied per lane.

An example of purification results for alpha-amylase II inhibitor from barley are presented in Table I. The yield of barley inhibitor was 239 mg of protein obtained from 1 kg of barley, cv. Bonanza. This yield is approximately 10-fold higher than that by other published procedures (Weselake et al, *Plant Physiol* (1983) 73:809-812). Purity of the barley inhibitor preparation was determined by SDS-PAGE, FIG. 2, and analytical isoelectric focusing (IEF), FIG. 3.

TABLE I

Purification of Alpha-Amylase Inhibitor

| Purification Step | Total Inhibitor (anti units) $\times 10^6$ | Total Protein (mg) | Specific Activity (anti units/mg) | Purification Factor (fold) | Yield % |
|---|---|---|---|---|---|
| Crude Extract | 16.24 | 17,729 | 916 | 1.0 | 100.0 |
| Crude Extract after pH Adjustment | 17.05 | 17,719 | 962 | 1.05 | 105.0 |
| Cu—IDA-Sepharose 6B | 13.14 | 390 | 33,692 | 36.8 | 80.9 |
| S-Sepharose | 11.00 | 239 | 46,025 | 50.2 | 67.7 |

Inhibitor Assay

Inhibitor assays were conducted at pH 8.0 buffer (0.04M Tris-HCl, $10^{-3}$M $CaCl_2$) and at 35° C. The Briggs assay for alpha-amylase (Briggs, *J Inst Brew* (1961) 67:427–431) was adapted to measure inhibitor activity during purification steps. 0.5 ml of appropriately diluted inhibitor solution was preincubated for 15 minutes with 0.5 ml of appropriately diluted wheat alpha-amylase II. Control digests without inhibitor were prepared. The reaction was started by addition 1 ml of beta-limit dextrin (0.65 mg/ml) and after 15 minutes stopped by addition 5 ml of acidified $I_2$-KI (0.05N HCl, 0.5 mg KI/ml, 0.05 mg $I_2$/ml). Loss of iodine-binding capacity was determined at 540 nm. One inhibitor unit was defined as the amount of inhibitor that inhibits one unit of alpha-amylase.

Preparation of Wheat Alpha-Amylase II

Total alpha-amylase from germinated wheat Neepawa was prepared basically according to Weselake and Hill, *Cereal Chem* (1983)60:98–101 with minor modifications. The crude extract was not treated with polyvinylpolypyrrolidone (PVP). Instead of *Bio-Gel P4 to separate cycloheptaamylose (CHA), *Bio-Gel P6 (200–400 mesh, Bio-Rad Laboratories, Mississauga, Ontario) was used.

Alpha-amylase II (alpha-amylase soenzymes with high isoelectric points, pI) was separated from the alpha-amylase I (isoenzymes with lower pI) using a 2.6×26 cm CM-*Sepharose column equilibrated with 0.02M sodium acetate buffer (pH 5.0, $10^{-3}$M $CaCl_2$). After sample application the column was subsequently washed with equilibration buffer, 0.08M sodium acetate (pH 5.1, $10^{-3}$M $CaCl_2$). Alpha-amylase II was eluted with a gradient including 100 ml of 0.2M sodium acetate buffer (pH 5.1, $10^{-3}$M $CaCl_2$) and 100 ml of 1M sodium acetate buffer (pH 5.1, $10^{-3}$M $CaCl_2$). Purity of alpha-amylase fractions was determined by isoelectric focusing followed by protein and enzymatic activity staining (Zawistowska et al, (1988) supra). High isoelectric point fractions containing alpha-amylase II were combined, concentrated in an Amicon cell equipped with 10,000 MW cut-off membrane and stored in the presence of 0.1% bovine serum albumin (BSA) at −40° C.

During all purification steps alpha-amylase was assayed by the Briggs method. A unit of activity was defined as the amount of enzyme required to change the optical density of a beta-limit dextrin solution from 0.6 to 0.4 in 100 minutes.

EXAMPLE 2

The base flour used in this example was a commercial "all purpose" flour milled from Canadian hard red spring wheat. Its protein and ash contents were 12.0% and 0.40% respectively, on a 14% moisture basis. In the standard amylograph test (AACC Approved Methods (Method 22-10), The Association, St. Paul, Minn. (1987)), it had a peak viscosity of 310 B.U. Its amylase activity, determined as taught by Kruger, J. E., et al, *Cereal Chem* (1981) 58:271–274, was 8.1 units.

The high alpha-amylase activity flour was prepared by adding an appropriate amount of malted barley flour (Diamalt II, Fleischmann) to lower the peak amylograph viscosity to 180 B.U. by increasing the alpha amylase Activity to 23.0 units. Alpha amylase inhibitor was prepared from barley, cv. Bonanza, by the procedure of Example 1.

Baking was done on a fully automated Japanese "Bread Bakery" (Panasonic, Model SD-BT-2N). The procedure used by this "bakery" is analogous to the Canadian "remix" baking test described in Irvine, G. N., et al, *Cereal Chem* (1960) 37:603–613, which is incorporated herein by reference. In this bread maker all steps starting from mixing ingredients and ending in baking are done automatically.

The baking formula used (Table II) was identical to that recommended in the Panasonic manual. For the baking experiments a commercial all-purpose flour having amylograph viscosity of 310 B.U. was used as a "control". Alpha-amylase level was increased artificially through the addition of malted barley flour to the "control" flour in a ratio of 1:400. The high alpha-amylase flour was characterized by the amylograph viscosity of 180 B.U. The barley inhibitor preparation was dissolved in water prior to mixing with all ingredients.

TABLE II

Basic Bread Formula

| | | | |
|---|---|---|---|
| Flour | 300 g | Butter | 11 g |
| Sugar | 17 g | Water | 200 ml |
| Milk powder | 6 g | Dry yeast (Firmapan) | 4.5 g |
| Salt | 5 g | | |

Baking results showed that addition of excess (more than required for normal baking) of alpha amylase produced the anticipated effect on bread quality, caving in of the top and the side walls and a more open crumb grain. The texture of the crumb was noticeable sticky instead of silky-smooth as in the control loaf. The sticky nature of the crumb and the tendency to ball up in the mouth was particularly noticeable during eating. In contrast, the "control" flour resulted in a regular shape loaf with a round top and relatively regular crumb structure.

Addition of the alpha amylase inhibitor as one of the bread ingredients completely neutralized the detrimental effect of excess alpha amylase. The size and appearance of the loaf were essentially the same as those of the control loaf. The original grain and texture were fully recovered.

These results indicate that an addition of the naturally alpha-amylase inhibitor isolated from barley to flour normally unsuitable for bread making makes possible the production of acceptable bread from flour made from sprout-damaged wheat.

EXAMPLE 3

Production of Polyclonal Antibodies to Alpha-Amylase Inhibitor

Polyclonal antibodies to alpha-amylase were produced in rabbits. A young female rabbit was immunized via intradermal injection. Purified alpha-amylase inhibitor was dissolved in deionized $H_2O$ at a concentration of 2 mg/ml of protein resulting in an antigen stock solution. Freund's complete adjuvant was mixed thoroughly with an equal volume of the stock solution. The mixture was administered to the rabbit intradermally in a shaved area on the lower back. The amount of 600 μg of antigen was received in the primary injection. Subsequent booster shots (600 μg each) were administered at 16, 28 and 32 days after the primary injection. Bleedings (5-10 ml) were taken between injections and the titer of serum determined. Serum collected prior to the primary injection and stored at −40° C. was used as a control. The rabbit was bled by cardiac puncture at 52 days after the primary injection and the serum retained at −40° C. for future analysis.

Immnoglobulin (IgG) fraction was isolated essentially according to Fahney (1967), in Methods in Immunology and Immunochemistry (Williams and Chase, eds.), p. 321, Academic Press, New York. Purification involved ammonium sulfate precipitation followed by ion-exchange chromatography on DEAE-Sephacel column (Pharmacia, Uppsala, Sweden). The unretained peak from the DEAE-Sephacel column containing the IgG fraction was concentrated on an Amicon cell using PM10 membrane, dialyzed against 0.9% NaCl overnight, filtered through 0.22 μm filter (Syrfil-MF, Nucleopore Corp.), and stored frozen at −40° C.

The titer of antibodies was determined by double-antibody assay using dot-blotting technique on a nitrocellulose membrane. As a second antibody, goat antirabbit horseradish peroxidase conjugate (available from Bio-Rad Laboratories (Canada) Ltd., Missassauga, Ontario) was used. Titers were approximately 1:10,000.

These antibodies are then used to probe a cDNA library of barley messenger RNA to isolate nucleotide sequences encoding the alpha-amylase inhibitor.

I claim:

1. A process for the preparation of a cereal protein which is an alpha-amylase inhibitor which process comprises (a) extracting cereal meal with an aqueous buffer having a pH range of about 5.5 to about 8 to provide an extract of crude inhibitor; and (b) purifying the extract of the crude inhibitor by immobilized metal affinity chromatography followed by ion exchange chromatography, said alpha-amylase inhibitor having the following physical and chemical characteristics:

it is a salt soluble protein with molecular weight of about 21,000 and isoelectric print at pH 7.2;

it inhibits wheat alpha-amylase II and subtilisin (alkaline protease from Bacillus subtilus); and it does not inhibit the human serine proteases trypsin and chymotrypsin.

2. The process of claim 1 wherein the cereal is barley.

3. The process of claim 1 wherein the aqueous buffer is Tris-HCl in a concentration of from about 0.05M to about 0.1M.

4. The process of claim 3 wherein the Tris-HCl buffer used has a concentration of about 0.05M.

5. The process of claim 1 wherein the aqueous buffer is a Tris-HCl buffer having a pH of about 5.5.

6. The process of claim 3 wherein the Tris-HCl buffer used for a concentration of about 0.05M and a pH of about 5.5.

7. The process of claim 1 wherein the immobilized metal affinity chromatography is carried out using a copper-IDA-non-ionic gel resin and the ion exchange chromatography is carried out using a sulphonate Sepharose gel resin.

* * * * *